United States Patent [19]

Mack

[11] Patent Number: 5,041,284
[45] Date of Patent: Aug. 20, 1991

[54] METHOD OF PREVENTING FROSTBITE

[76] Inventor: Alphonso L. Mack, 9 McCormick Pl., Bloomfield, Conn. 06002

[21] Appl. No.: 404,742

[22] Filed: Sep. 8, 1989

[51] Int. Cl.$^5$ .......................... A61K 7/32; A61K 7/38; A61K 7/48; A61K 9/12

[52] U.S. Cl. ........................................ 424/65; 424/47; 514/827; 514/828; 514/930

[58] Field of Search .................. 424/65; 514/827, 828, 514/930

[56] References Cited

U.S. PATENT DOCUMENTS 4,879,116 11/1989 Fox et al. ............................ 514/827

OTHER PUBLICATIONS

"Antiperspirant Drug products for Over-the-Counter Human Use; Tentative Final Monograph (Proposed Rule)", Federal Register, vol. 47, No. 162 (1982).
Beeson et al., Cecil Loeb Textbook of Medicine, 1971, pp. 1133 and 1134.

Primary Examiner—Dale R. Ore
Attorney, Agent, or Firm—Fishman, Dionne & Cantor

[57] ABSTRACT

A method for preventing frostbite of body portions is disclosed. The method includes applying an antiperspirant composition to the body portion and covering the body portion with a thermally insulating material.

10 Claims, No Drawings

METHOD OF PREVENTING FROSTBITE

TECHNICAL FIELD

This invention relates to the protection of portions of a human body from damage to exposure to a low temperature environment.

BACKGROUND OF THE INVENTION

Exposure of the human body to a low temperature environment may result in discomfort and, under extreme circumstances, localized tissue destruction, i.e. "frostbite", to inadequately protected bodily extremities. Hands and feet are particularly susceptable to frostbite due to their high surface area to volume ratio.

It is desirable that any thermal protection for the hands and feet not be unduly restrictive. Conventional methods which are adequate to protect hands and feet from low temperature damage can be cumbersome, particularly when the wearer is engaged in cold weather pursuits which require intermittent vigorous physical activity, such as skiing and mountaineering.

DISCLOSURE OF THE INVENTION

A method for preventing frostbite to a portion of the human body is disclosed. The method includes applying an antiperspirant composition to the body portion to be protected and covering the body portion with a thermally insulating material. The method allows the use of a relatively thin insulating layer, since the insulating properties of the insulating material are not compromised by perspiration absorbed from the body portion.

DESCRIPTION OF THE PREFERRED EMBODIMENT

The method of the present invention includes applying an antiperspirant composition. Suitable antiperspirant compositions comprise any topically applied compositions effective in reducing perspiration from human skin. Suitable antiperspirant compositions preferably include an active ingredient chosen from the group consisting of aluminum bromohydrate, aluminum chlorhydrate, aluminum dichlorhydrate, aluminum sesquichlorohydrex, aluminum sesquichlorohydrex PEG, aluminum chloride, aluminum sulfate, buffered aluminum sulfate, potassium alum, and sodium aluminum chlorohydroxy lactate. The active ingredient may be included in a cream, a lotion, a waxy solid, or a liquid solution. Preferably the antiperspirant composition includes from 2 wt % to 25 wt % of the active ingredients.

Suitable antiperspirant compositions may include physiologically acceptable diluents or carriers such as water, an alcohol, or mixtures thereof, water and oil emulsions, as well as additives such as buffers and solubility modifiers. Suitable additives include glycine buffers, glycine salts and glycol buffers. Liquid compositions may further include a propellant, such as butane or isobutane so that the composition may be applied as an aerosol spray. Conventional antiperspirant compositions are available from a number of commercial sources and are suitable for use as the antiperspirant composition of the present invention.

The antiperspirant composition is applied to the body portion in an amount sufficient to reduce the perspiration rate exhibited by the body portion to which it is applied. If a diluent is included in the composition, the diluent is allowed to evaporate prior to covering the body portion with the insulating layer.

The method of the present invention includes covering the body portion with a layer of thermally insulating material. The thermally insulating material of the present invention may be any material that reduces the rate of heat transfer from the covered body portion to it surroundings. Preferred insulating materials include natural or synthetic fibers, polymeric open celled foams and polymeric closed cell foams.

In preferred embodiments, the method includes covering the insulating material with a moisture barrier layer. The moisture barrier layer of the present invention may comprise of any material that provides resistance to moisture transport. Suitable moisture barrier layers include water repellent layers and moisture impervious layers. Suitable water repellent layers include layers of natural or synthetic fabric or of leather that have been treated with conventional water repellent compositions or laminated with porous polymeric films, e.g. Gore ® laminates. Suitable moisture impervious layers include polymeric layers, e.g. polyethylene layers and polyvinylchloride layers.

Convenient sources of suitable insulating layers and moisture barrier layers include conventional outdoor apparel such as gloves, mittens, socks, shoes, boots and ski boots.

Absorbed moisture reduces the insulating ability of the insulating material. The advantage of covering the insulating layer with a water repellent or moisture impervious layer is that the insulating properties of the insulating material are not compromised by moisture absorbed from the environment. However, water repellent layers reduce the rate at which perspiration from the protected body portion is transferred through the insulation and is evaporated to the environment. Moisture impervious layers prevent evaporation of perspiration from the insulating layer. It will be appreciated that in conventional protective methods, the use of moisture barrier layers may ultimately prove to be counterproductive since the moisture barrier covered insulating layer eventually becomes ineffective due to absorbed perspiration. The above situation may be further aggravated by intermittent vigorous physical activity. Intermittent vigorous physical activity is any activity which includes alternating periods of vigorous physical activity and periods of relative inactivity. The periods of vigorous activity may be characterized by excessive heat generation and a high persperation rate. The periods of relative inactivity may be characterized by rapid heat loss.

The present invention offers advantages in each of the preferred embodiments since the present invention reduces the perspiration rate and thereby reduces the quantity of perspiration available for absorbtion by the insulating material. The present invention offers particular advantages in situations involving intermittent vigorous physical activity in low temperature environments. The method allows the use of a relatively thin insulating layer. The thin insulating layer mitigates overheating during vigorous activity, yet is protective during periods of relative inactivity since its insulating properties have not been compromised by absorbed moisture.

EXAMPLE 1

A 5 second spray of an aerosol composition comprising 25% by weight aluminum chlorhydrate in a mixture of 50 vol % water and 50 vol % ethanol is applied to a subjects right foot. The solution is allowed to air dry. The subjects right and left feet are covered with socks and ski boots. The subject engages in downhill skiing for several hours under subfreezing conditions. After the several hours of activity, the subjects right foot is warm and dry while the subjects left foot is damp and cold.

EXAMPLE 2

A 5 second spray of an aerosol composition comprising 25% by weight aluminum chlorhydrate in a mixture of 50 vol % water and 50 % vol ethanol is applied to a subjects left hand. The solution is allowed to air dry. Each of a pair of gloves is weighed. The subjects right and left hands are then covered with the gloves. The subject engages in activity in a low temperature environment. After three hours of activity, the left hand is dry and warm while the right hand is cold and damp. The gloves are removed and weighed. The right glove has significantly increased in weight while the left glove has not significantly increased in weight indicating the presence of absorbed perspiration in the right glove.

The method of the present invention prevents frostbite of body portions by reducing the perspiration that may be absorbed by the thermally insulating material covering the body portion, so that the thermally insulating properties of the material are not compromised by absorbed perspiration.

While preferred embodiments have been shown and described, various modifications and substitutions may be made thereto without departing from the spirit and scope of the invention. Accordingly, it is to be understood that the present invention has been described by way of illustrations and not limitations.

What is claimed is:

1. A method for preventing frostbite of a portion of a human body wherein the body is exposed to a low temperature environment comprising:
   applying an effective amount antiperspirant composition to the body portion,
   covering the body portion with a thermally insulating material.

2. The method of claim 1, further comprising covering the insulating material with a moisture barrier layer.

3. The method of claim 1, wherein the body portion comprises a foot.

4. The method of claim 3, wherein the layer of thermal insulating material comprises a sock.

5. The method of claim 1, wherein the body portion comprises a hand.

6. The method of claim 1, wherein the insulating material comprises a glove or mitten.

7. The method of claim 2, wherein the moisture barrier layer comprises a ski boot.

8. The method of claim 1, wherein the antiperspirant composition is chosen from the group consisting of aluminum bromohydrate, aluminum chlorhydrate, aluminum dichlorhydrate, aluminum sesquichlorohydrex, aluminum sesquichlorohydrex PEG, aluminum chloride, aluminum sulfate, buffered aluminum sulfate, potassium alum, and sodium aluminum chlorohydroxy lactate.

9. The method of claim 1, wherein the antiperspirant composition comprises a solution of from 2 wt % to 25wt % of a compound chosen from the group consisting of aluminum bromohydrate, aluminum chlorhydrate, aluminum dichlorhydrate, aluminum sesquichlorohydrex, aluminum sesquichlorohydrex PEG, aluminum chloride, aluminum sulfate, buffered aluminum sulfate, potassium alum, and sodium aluminum chlorohydroxy lactate and 75wt % to 95wt % of an aqueous solvent.

10. The method of claim 10, wherein the aqueous solvent further comprises an alcohol and a buffer compound.

* * * * *